United States Patent
Chapuis

(10) Patent No.: US 8,481,013 B2
(45) Date of Patent: Jul. 9, 2013

(54) COMPOUNDS HAVING SANDALWOOD ODORS

(75) Inventor: Christian Chapuis, Mies (CH)

(73) Assignee: Firmenich SA, Geneav (CH)

( * ) Notice: Subject to any disclaimer, the term of this patent is extended or adjusted under 35 U.S.C. 154(b) by 133 days.

(21) Appl. No.: 13/123,776

(22) PCT Filed: Nov. 18, 2009

(86) PCT No.: PCT/IB2009/055142
§ 371 (c)(1),
(2), (4) Date: Apr. 12, 2011

(87) PCT Pub. No.: WO2010/061316
PCT Pub. Date: Jun. 3, 2010

(65) Prior Publication Data
US 2011/0195038 A1    Aug. 11, 2011

(30) Foreign Application Priority Data
Nov. 26, 2008 (WO) .................. PCT/IB2008/054962

(51) Int. Cl.
| | |
|---|---|
| *A61K 8/34* | (2006.01) |
| *A61L 9/01* | (2006.01) |
| *A61Q 13/00* | (2006.01) |
| *C07C 31/137* | (2006.01) |
| *C07C 33/025* | (2006.01) |
| *D21H 17/06* | (2006.01) |

(52) U.S. Cl.
USPC ............ 424/65; 424/76.2; 162/158; 510/104; 512/14; 514/772; 568/819

(58) Field of Classification Search
None
See application file for complete search history.

(56) References Cited

U.S. PATENT DOCUMENTS
4,052,341 A * 10/1977 Naipawer et al. .................. 512/2
5,707,961 A    1/1998 Bajgrowicz et al. ............ 512/17

FOREIGN PATENT DOCUMENTS
| | | |
|---|---|---|
| DE | 43 40 353 A1 | 6/1995 |
| EP | 0 743 297 B1 | 11/1996 |
| EP | 0801049 | * 10/1997 |
| WO | WO9311094 | * 6/1993 |

OTHER PUBLICATIONS

International Search Report and Written Opinion mailed Jun. 4, 2010 for application No. PCT/IB2009/055142 filed Nov. 18, 2009.
Chapuis et al., "Preparation of Optically Active Cyclohexenones: Chirons for the Lipophilic Moiety of Flowery- and Woody-like Odorant Ketones," Helvetica Chimca Acta, 76:535-544 (1993).
Julia et al., "Synthèse d'χ- et γ-cyclohomocitrals substitutés," C.R.S. Acad. Sci., 252:2893-2895 (1961).
Julia et al., "Synthèse d'χ- et γ-cyclohomocitrals substitutés, des cétones et des alcools correspondants," Bull. Soc. Chim. Fr., 1952-1959 (1962).
Kawanobe et al., "Syntheses of (±)-cis-γ-Irone and Its Related Compounds," Agric. Biol. Chem., 51(3):791-796 (1987).

* cited by examiner

Primary Examiner — David J Blanchard
Assistant Examiner — Thurman Wheeler
(74) Attorney, Agent, or Firm — Winston & Strawn LLP

(57) ABSTRACT

Sandalwood perfuming ingredients that are 2-[perhydro-trialkyl-2-naphthalenylidene]-1-propanol or propanal derivatives of the formula

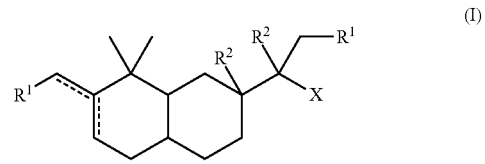

wherein one dotted line represents a carbon-carbon single bond and the other a carbon-carbon single bond or double bond; X represents a $CH_2OH$ group or a CHO group; each $R^1$ represents a hydrogen atom or a methyl group; and the $R^2$, taken separately, represent each a hydrogen atom or the two $R^2$ groups, taken together, represent a $CH_2$ group or a carbon-carbon double bond; and said compound is in the form of any one of its stereoisomers or a mixture thereof, along with the use of such compound(s) in perfuming compositions or articles in the perfumery industry.

16 Claims, No Drawings

COMPOUNDS HAVING SANDALWOOD ODORS

This application is a 371 filing of International Patent Application PCT/IB2009/055142 filed Nov. 18, 2009.

TECHNICAL FIELD

The present invention relates to the field of perfumery. More particularly, it concerns some 2-[perhydro-trialkyl-2-naphthalenylidene]-1-propanol or propanal derivatives which possess sandalwood odors. The present invention concerns the use of said compounds in the perfumery industry as well as the compositions or articles containing said compounds.

PRIOR ART

To the best of our knowledge, all the compounds of the present invention are new.

Synthetic sandalwood odorants are particularly important for the perfumery industry, in particular because the supply of natural sandalwood essence is constantly declining Although the perfumer's palette already possesses some sandalwood odorants (e.g. 2-ethyl-4-(2,2,3-trimethyl-3-cyclopenten- 1-yl)-2-buten- 1-ol or 2,3,3-trimethyl-bicyclo[2.2.1]heptan-2-ol), all of them are structurally very different from those of the present invention. Therefore, said prior art sandalwood odorants do not suggest or anticipate the organoleptic properties of the present invention's compounds, because none of the prior art compounds possess a naphthalene skeleton.

DESCRIPTION OF THE INVENTION

We have now surprisingly discovered that a compound of formula

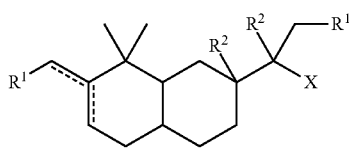

(I)

wherein one dotted line represents a carbon-carbon single bond and the other a carbon-carbon single bond or double bond;

X represents a CH$_2$OH group or a CHO group; each R$^1$, taken separately, represents a hydrogen atom or a methyl group; and the R$^2$, taken separately, represent each a hydrogen atom, or the two R$^2$ groups, taken together, represent a CH$_2$ group or a carbon-carbon double bond;

and said compound is in the form of any one of its stereoisomers or a mixture thereof; can be used as perfuming ingredient, for instance to impart odor notes of the sandalwood type.

For the sake of clarity, by the expression "the two R$^2$ groups, taken together, represent . . . a carbon-carbon double bond", or the similar, it is meant the normal meaning understood by a person skilled in the art, i.e. that the whole bonding between the carbon atoms bearing said R$^2$ groups is a carbon-carbon double bond.

For the sake of clarity, by the expression "one dotted line represents a carbon-carbon single bond and the other a carbon-carbon single bond or double bond", or the similar, it is meant the normal meaning understood by a person skilled in the art, i.e. that the whole bonding (solid and dotted line) between the carbon atoms connected by said dotted line is a carbon-carbon single or double bond.

According to a particular embodiment of the invention, said compound (I) is one of formula

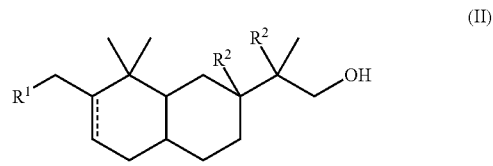

(II)

wherein the dotted line represents a carbon-carbon single bond or double bond;

R$^1$ represents a hydrogen atom or a methyl group; and the two R$^2$ groups, taken together, represent a CH$_2$ group or a carbon-carbon double bond.

According to a specific aspect of the invention, in any one of the above embodiments the dotted lines represent a carbon-carbon single bond.

According to another particular embodiment of the invention, said compound (I) is of formula

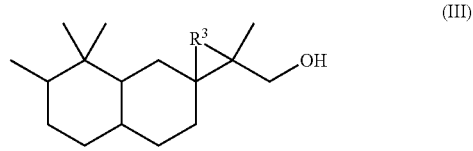

(III)

wherein R$^3$ represents a CH$_2$ group or a carbon-carbon bond.

As specific, but non-limiting, examples of the invention's compounds, one may cite 2- [perhydro-7,8,8-trimethyl-2-naphthalenylidene]-1-propanol. In particular, its stereoisomer (2E)-2-[(4aR,7S ,8aR)-perhydro-7,8,8-trimethyl-2-naphthalenylidene]-1-propanol possesses a nice and well balanced sandalwood and woody note, which is very natural and typical of sandalwood milk.

The odor of this compound distinguishes itself from the other known sandalwood odorants, and in particular from those which are derivatives of campholenic aldehyde, by having a much more natural and much more pronounced sandalwood milk, sandalwood Mysore connotation. In fact the odor of said invention's compound resembles very closely the odor of β-santalol, which is the key component of the natural sandalwood Mysore essence. Furthermore, to the best of our knowledge, the invention's compound possesses the most substantive sandalwood note known, i.e. more than two months, which is by far superior to the substantivity of the currently used synthetic sandalwood odorants.

As other specific, but non-limiting, examples of the invention's compounds, one may cite the following ones in Table 1:

TABLE 1

Invention's compounds and their odor properties

| Compound structure and name | Odor notes |
|---|---|
| 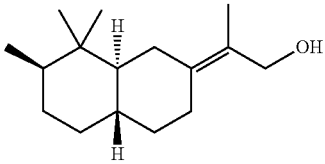 [SMILES: C/C(CO)=C1/CC[C@@H]2CC[C@@H](C)C(C)(C)[C@H]2C1]<br>(2E)-2-[(4aS,7R,8aS)-perhydro-7,8,8-trimethyl-2-naphthalenylidene]-1-propanol | Woody, sandalwood, milky, fruity slightly smoky |
| 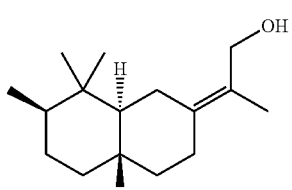<br>(2Z)-2-[(4aS,7R,8aS)-perhydro-7,8,8-trimethyl-2-naphthalenylidene]-1-propanol | Woody, sandalwood, milky; sandalwood milk |
| 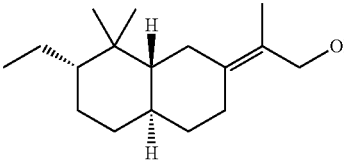<br>Mixture of (2E)-2-[(4aR,7S,8aR)-7-ethyl-8,8-dimethyloctahydro-2(1H)-naphthalenylidene]-1-propanol and (2E)-2-[(4aS,7S,8aS)-7-ethyl-8,8-dimethyloctahydro-2(1H)-naphthalenylidene]-1-propanol | Sandalwood, milky odor |
| 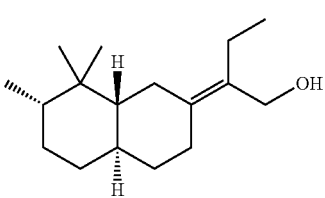 [SMILES: CC/C(CO)=C1/CC[C@H]2CC[C@H](C)C(C)(C)[C@@H]2C1]<br>Mixture of (2E)-2-[(4aR,7S,8aR)-7,8,8-trimethyloctahydro-2(1H)-naphthalenylidene]-1-butanol and (2E)-2-[(4aS,7S,8aS)-7,8,8-trimethyloctahydro-2(1H)-naphthalenylidene]-1-butanol | Sandalwood, natural, weak, substantive |

TABLE 1-continued

Invention's compounds and their odor properties

| Compound structure and name | Odor notes |
|---|---|
| 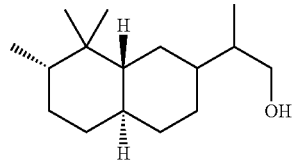 [SMILES: CC(CO)C1CC[C@H]2CC[C@H](C)C(C)(C)[C@@H]2C1]<br>2-((4aS,7S,8aR)-7,8,8-trimethyldecahydronaphthalen-2-yl)propan-1-ol | Sandalwood |

According to a particular embodiment of the invention, the compounds of formula (I) are: 2-[perhydro-7,8,8-trimethyl-2-naphthalenylidene]-1-propanol, and in particular (2E)-2-[(4aR,7S ,8aR)-perhydro-7,8,8-trimethyl-2-naphthalenylidene]-1-propanol or (2E)-2-[(4aS,7R,8 aS)-perhydro-7,8,8-trimethyl-2-naphthalenylidene]-1-propanol.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredients, are also an object of the present invention.

Therefore, an object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids : Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric softeners, fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 25% by weight, or even more, of the compounds of the invention based on the weight of the composition into which they are incorporated. Concentrations lower than these, such as in the order of 0.001% to 10% by weight, can be used when these compounds are incorporated into perfumed articles, percentage being relative to the weight of the article.

The invention's compounds can be prepared according to a method wherein the ketone

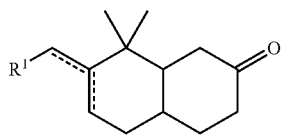

(K)

obtained according to any standard method known in the art, and of which one specific example is described in the Examples herein below, and wherein $R^1$ and the dotted lines have the same meaning as in formula (I);

is reacted under Wittig conditions (with e.g. triethylphosphonopriopionate or butyrate) to produce the ester

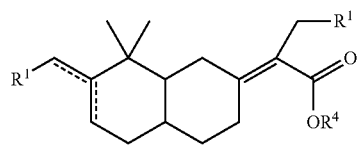

(E)

wherein $R^1$ and the dotted lines have the same meaning as in formula (I), and $R^4$ represents a $C_{1-4}$ alkyl group.

Ester (E) can be subsequently concerted into a product of formula (I) according to standard methods such as ester reduction, C=C hydrogenation or cyclopropanation.

Specific examples of such methodology are provided in the Examples herein below.

The compounds of formula (I) are new compounds, as well as some of the intermediates used in their preparations (in particular the esters (E)). Therefore, another object of the present invention is a compound of formula

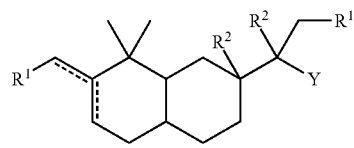

(IV)

wherein the dotted lines, $R^1$ and $R^2$ are defined as in formula (I) and

Y represents a $CH_2OH$, CHO or $COOR^4$ group, $R^4$ being a $C_{1-4}$ alkyl group; and said compound is in the form of any one of its stereoisomers or a mixture thereof.

According to a particular embodiments said compound (IV) is of formula

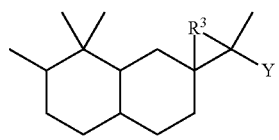

(V)

wherein $R^3$ is defined as in formula (III) and Y represents $CH_2OH$, CHO or $COOR^4$ group, $R^4$ being a $C_{1-4}$ alkyl group.

EXAMPLES

The invention will now be described in further detail by way of the following examples, wherein the abbreviations have the usual meaning in the art, the temperatures are indicated in degrees centigrade (° C.) ; the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I):

A general pathway is showed in the scheme herein below:

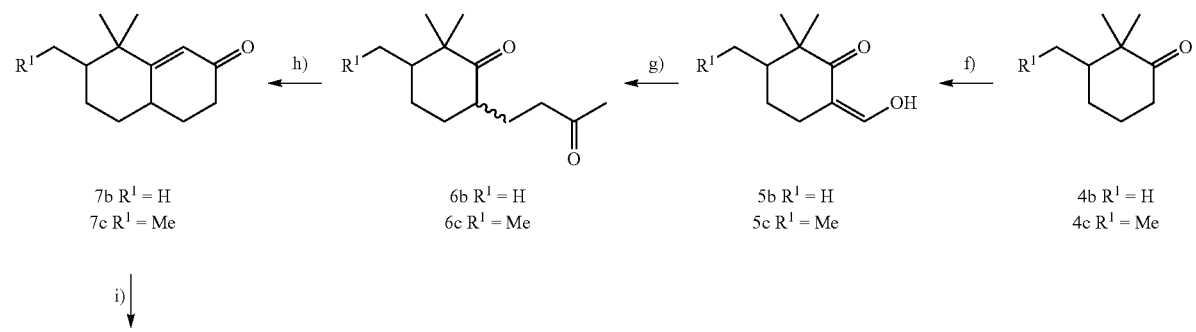

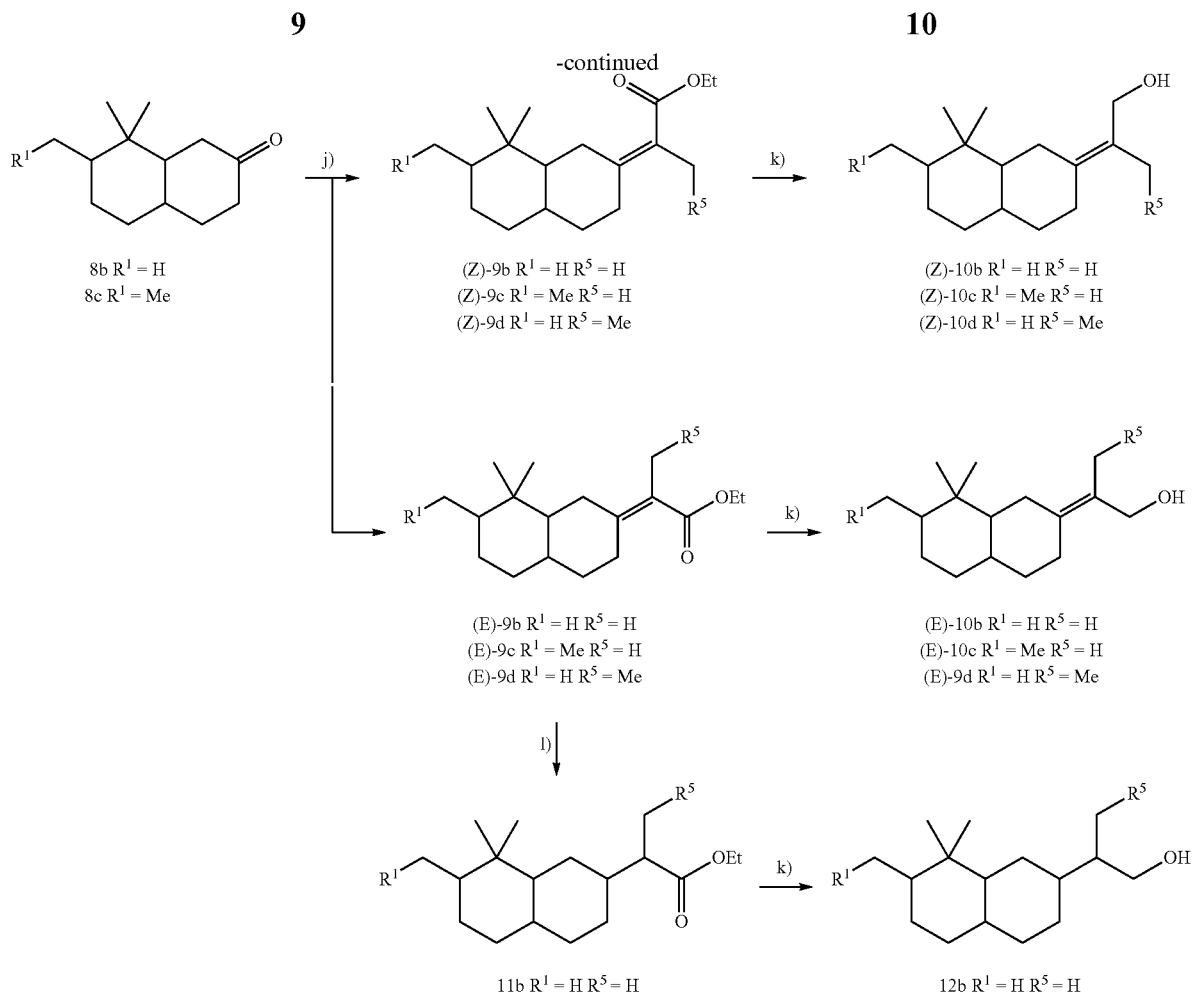

f) HCO$_2$Et, MeONa, Et$_2$O; g) Me-vinyl-ketone, Me$_3$N, DMAP, THF, 40°; h) KOH, EtOH; i) Li, NH$_3$, tBuOH, Et$_2$O; j) EtONA, EtOH, pentane, (EtO)$_2$P(O)CH(Me)CO$_2$Et; k) LiAlH$_4$, Et$_2$O; l) H$_2$, PD/C, ETOH.

Experimental Part a) (6Z)-6-(Hydroxymethylene)-2,2,3-trimethylcyclohexanone: 5b (For the racemate, see S. Julia et al. *Bull. Soc. Chim. Fr.* 1962, 1952; S. Julia et al. *C. R. S. Acad. Sci.* 1961, 252, 2893; Kawanobe et al. *Agric. Biol. Chem.* 1987, 51, 791).

(+)-(3R,6Z)-6-(Hydroxymethylene)-2,2,3-trimethylcyclohexanone: (+)-5b:

MeONa (11.4 g, 0.2 mol) was added portionwise at 5° C. to a solution of ethyl formate (25.3 g, 0.33 mol) in Et$_2$O (50 ml). A solution of (−)-4b (14 g, 0.1 mol; C. Chapuis, R. Brauchli, W. Thommen, *Helv. Chim. Acta* 1993, 76, 535) in Et$_2$O (100 ml) was added dropwise in 1 hour. After 2 additional hours at 20°, the reaction mixture was poured onto ice. AcOH (20 ml) was added and the acidic aqueous phase was washed with Et$_2$O. The organic phase was washed with brine (2×), NaHCO$_3$, brine, dried (Na$_2$SO$_4$), filtered, concentrated and bulb-to-bulb distilled to afford pure (+)-5b in 86% yield.

Bp: 80°/0.3 mbar. $\alpha_D^{20}$ =+43.83 neat.

$^1$H-NMR: 8.74 (s, 1H); 2.38 (s, OH); 2.37 (m, 1H); 2.31 (m, 1H); 1.65 (m, 1H); 1.58 (m, 1H); 1.45 (m, 1H); 1.21 (s, 3H); 1.06 (s, 3H); 0.94 (d, J=7, 3H).

$^{13}$C-NMR: 190.0 (s); 189.4 (d); 106.7 (s); 40.8 (s); 38.0 (d); 27.0 (t); 24.9 (q); 22.6 (t); 20.7 (q); 15.8 (q). MS: 168 (75, M+), 140 (19), 125 (100), 107 (22), 97 (15), 83 (86), 70 (29), 55 (44), 43 (26), 41 (37).

(−)-(3S,6Z)-6-(Hydroxymethylene)-2,2,3-trimethylcyclohexanone: (−)-5b

As above using (+)-4b (C. Chapuis, R. Brauchli, W. Thommen, *Helv. Chim. Acta* 1993, 76, 535). (−)-5b was obtained in 88% yield. $\alpha_D^{20}$ =−44.63.

b) (6Z)-6-(Hydroxymethylene)-2,2-dimethyl-3-ethylcyclohexanone: 5c (+)-(3R,6Z)-6-(Hydroxymethylene)-2,2-dimethyl-3-ethylcyclohexanone: (+)-5c MeONa (52.92 g, 0.98 mol) was added portionwise at 5° C. to a solution of ethyl formate (119.66 g, 1.62 mol) in Et$_2$O (200 ml). A solution of (−)-4c (75.5 g, 0.49 mol; C. Chapuis, R. Brauchli, W. Thommen, *Helv. Chim. Acta* 1993, 76, 535) in Et$_2$O (400 ml) was added dropwise in 1 h. After 12 additional h. at 20°, C. the reaction mixture was poured onto ice. AcOH (80 ml) was added and the acidic aqueous phase was washed with Et$_2$O. The organic phase was washed with brine (2×), NaHCO$_3$, brine, dried (Na$_2$SO$_4$), filtered, concentrated and bulb-to-bulb distilled to afford pure (+)-5c in 98% yield.

Bp: 120° C./0.1 mbar. $\alpha_D^{20}$ =+8.2 neat.

$^1$H-NMR: 8.76 (s, 1H); 2.41 (s, OH); 2.38 (m, 1H); 2.28 (m, 1H); 1.86 (m, 1H); 1.57 (m, 1H); 1.31 (m, 1H); 1.22 (s, 3H); 1.20 (m, 1H); 1.07 (m, 1H); 1.06 (s, 3H); 0.96 (t, 3H).

$^{13}$C-NMR: 190.0 (s); 189.5 (d); 106.9 (s); 45.6 (s); 41.1 (s); 24.7 (q); 22.9 (t); 22.7 (t); 22.1 (t); 21.0 (q); 12.8 (q). MS: 182 (75, M+.), 154 (19), 139 (100), 125 (42), 111 (27), 97 (68), 83 (30), 69 (53), 55 (86), 43 (44), 41 (57).

(−)-(3S,6Z)-6-(Hydroxymethylene)-2,2-dimethyl-3-ethylcyclohexanone: (−)-5c

As above using (+)-4c (C. Chapuis, R. Brauchli, W. Thommen, *Helv. Chim. Acta* 1993, 76, 535). (−)-5c was obtained in 98% yield. $\alpha_D^{20}$ =−12.67.

c) 2,2,3-Trimethyl-6-(3-oxobutyl)cyclohexanone:6b (−)-(3R)-2,2,3-Trimethyl-6-(3-oxobutyl)cyclohexanone: (−)-6b A mixture of (+)-5b (13 g, 77 mmol), methylvinylketone (11.8 g, 154 mmol), Et$_3$N (4.7 g, 47 mmol and DMAP (0.2 g) in THF (100 ml) was heated at 40° C. for 48 hours. The cold reaction mixture was concentrated and MeOH (200 ml) was added, followed by K$_2$CO$_3$ (20 ml, 1M aqueous solution, 20 mmol). This mixture was heated at reflux for 20 hours. The cold solution was concentrated, diluted with Et$_2$O, washed with brine (3×), dried (Na$_2$SO$_4$), filtered, concentrated, and bulb-to-bulb distilled to afford pure (−)-6b in 87% yield as a 3:2 trans/cis mixture.

Bp: 90° C./0.3 mbar. $\alpha_D^{20}$ =−8.3.

$^1$H-NMR: Major 2.55 (m, 2H); 2.40 (m,1H); 2.13 (s, 3H); 1.90 (m, 3H); 1.60 (m, 2H);

1.47 (m, 2H); 1.04 (s, 3H); 1.00 (s, 3H); 0.95 (d, J=7, 3H). Minor 2.64 (m, 2H); 2.20 (m, 1H); 2.13 (s, 3H); 1.98 (m, 3H); 1.64 (m, 2H); 1.47, (m, 1H); 1.30 (m, 1H); 1.24 (s, 3H); 0.98 (s, 3H); 0.84 (d, 3H).

$^{13}$C-NMR: Major 216.9 (s); 209.2 (s); 48.8 (s); 44.5 (t); 43.3 (d); 33.4 (d); 30.2 (q); 29.4 (t); 26.7 (t); 22.4 (2q); 22.0 (t); 15.7 (q). Minor 217.1 (s); 209.2 (s); 49.2 (s); 42.3 (d); 41.4 (t); 33.4 (d); 29.9 (t); 28.0 (q); 26.7 (t); 24.1 (2q); 18.9 (t); 15.9 (q).

(+)-(3S)-2,2,3-Trimethyl-6-(3-oxobutyl)cyclohexanone: (+)-6b

As above using (−)-5b. (+)-6b was obtained in 92% yield. $a_D^{20}$ =+6.88.

d) 2,2-dimethyl-3-ethyl-6-(3-oxobutyl)cyclohexanone: 6c (−)-(3R)-2,2-dimethyl-3-ethyl-6-(3-oxobutyl)cyclohexanone: (−)-6c A mixture of (+)-5c (80 g, 440 mmol), methylvinylketone (61.6 g, 880 mmol), Et$_3$N (26.7 g, 264 mmol and DMAP (1.12 g) in THF (560 ml) was heated at 40° C. for 8 hours. The cold reaction mixture was concentrated and MeOH (1120 ml) was added, followed by K$_2$CO$_3$ (112 ml, 1M aqueous solution). This mixture was heated at reflux for 3 hours. The cold solution was concentrated, diluted with Et$_2$O, washed with brine (3×), dried (Na$_2$SO$_4$), filtered, concentrated, and bulb-to-bulb distilled to afford pure (x)-6c in 99% yield as a 7:3 trans/cis mixture. Bp: 160° C./0.1 mbar. $\alpha_D^{20}$ =−15.5.

$^1$H-NMR: Major 2.55 (m, 3H); 2.40 (m, 1H); 2.13 (s, 3H); 1.90 (m, 3H); 1.53 (m, 1H); 1.47 (m, 3H); 1.23 (m, 1H); 1.06 (s, 3H); 1.00 (s, 3H); 0.92 (t, J=7, 3H). Minor 2.62 (m, 3H); 2.13 (s, 3H); 2.05 (m, 1H); 1.90 (m, 3H); 1.61 (m, 1H); 1.47 (m, 3H); 1.24 (s, 3H); 1.23 (m, 1H); 0.99 (s, 3H); 0.85 (t, J=7, 3H).

$^{13}$C-NMR: Major 216.8 (s); 209.3 (s); 50.7 (d); 48.9 (s); 44.8 (d); 41.4 (t); 33.4 (t); 29.8 (q); 26.3 (t); 24.1 (q); 22.8 (q); 22.3 (t); 21.5 (t); 13.0 (q). Minor 217.6 (s) ; 209.3 (s) ; 50.7 (d) ; 49.2 (s) ; 44.3 (d) ; 41.4 (t) ; 33.4 (t) ; 28.9 (t) ; 26.9 (q) ; 24.1 (q) ; 22.4 (t) ; 20.7 (t) ; 19.6 (q) ; 12.4 (q).

(+)-(3S)-2,2-dimethyl-3-ethyl-6-(3-oxobutyl)cyclohexanone: (+)-6c

As above using (−)-5c. (+)-6c was obtained in 99% yield. $a_D^{20}$=+15.1.

e) 7,8,8-Trimethyl-4,4a,5,6,7,8-hexahydro-2(3H)-naphthalenone : 7b (−)-(4aS,7R)-7,8,8-Trimethyl-4,4a,5,6,7,8-hexahydro-2 (3H)-naphthalenone: (−)-7b A mixture of (−)-6b (8.25 g, 39 mmol), KOH (4.0 g, 71 mmol) in EtOH (160 ml), was stirred at 20° C. for 2 hours before to be poured onto saturated NH$_4$Cl and extracted with Et$_2$O. The organic phase was washed with brine, dried (Na$_2$SO$_4$), filtered, concentrated and bulb-to-bulb distilled to afford pure (−)-7b in 90% yield as a 3:7 cis/trans (4aR,7R)1 (4aS,7R) mixture. Bp: 110° C./0.3 mbar. oc$_D^{20}$ =−38.5.

$^1$H-NMR: Major 5.97 (s, 1H); 2.52 (m, 1H); 2.36 (m, 1H); 2.28 (m, 2H); 2.11 (m, 1H); 1.89 (m, 1H); 1.68-1.30 (m, 4H); 1.13 (s, 3H); 0.99 (s, 3H); 0.94 (d, J=7, 3H). Minor 5.95 (s, 1H); 2.56 (m, 1H); 2.40 (m, 1H); 2.24 (m, 2H); 2.08 (m, 1H); 1.73 (m, 1H); 1.68-1.30 (m, 4H); 1.22 (s, 3H); 1.09 (s, 3H); 0.86 (d, J=7, 3H).

$^{13}$C-NMR: Major 201.3 (s); 175.3 (s); 121.5 (d); 41.7 (d); 40.7 (s); 35.3 (t); 36.6 (d); 30.4 (t); 29.8 (t); 29.1 (t); 25.1 (q); 21.0 (q); 16.4 (q). Minor 200.4 (s); 173.3 (s); 123.8 (d); 41.7 (d); 40.4 (s); 34.2 (t); 34.4 (d); 30.4 (t); 29.7 (t); 29.0 (t); 28.0 (q); 26.0 (q); 15.9 (q).

(+)-(4aR,7S)-7,8,8-Trimethyl-4,4a,5,6,7,8-hexahydro-2 (3H)-naphthalenone: (+)-7b As above using (+)-6b. (+)-7b was obtained in 70% yield. $\alpha_D^{20}$ =+44.15.

f) 8,8-dimethyl-7-ethyl-4,4a,5,6,7,8-hexahydro-2(3H)-naphthalenone: 7c (−)-(4aS,7R)-8,8-dimethyl-7-ethyl-4,4a,5,6,7,8-hexahydro-2(3H)-naphthalenone: (−)-7c A mixture of (−)-6c (97.0 g, 433 mmol), KOH (43.65 g, 779 mmol) in EtOH (970 ml), was stirred at 20° C. for 24 hours before to be poured onto sat. NH$_4$Cl and extracted with Et$_2$O. The organic phase was washed with brine, dried (Na$_2$SO$_4$), filtered, concentrated and bulb-to-bulb distilled to afford pure (−)-7c in 94% yield as a 3:7 cis/trans (4aR,7R)1 (4aS,7R) mixture. Bp: 160° C./0.1 mbar. $\alpha_D^{20}$ =−68.3 neat.

$^1$H-NMR: Major 5.98 (s, 1H); 2.53 (m, 1H); 2.35 (m, 1H); 2.28 (m, 1H); 2.08 (m, 1H); 1.93 (m, 2H); 1.64 (m, 3H); 1.30 (m, 1H); 1.15 (s, 3H); 1.06 (m, 2H); 0.99 (s, 3H); 0.92 (d, J=7, 3H). Minor 5.93 (s, 1H); 2.60 (m, 1H); 2.39 (m, 1H); 2.24 (m, 1H); 2.12 (m, 1H); 1.87 (m, 1H); 1.72 (m, 1H); 1.51 (m, 2H); 1.40 (m, 1H); 1.33 (m, 1H); 1.24 (m, 3H); 1.12 (m, 3H); 1.06 (m, 2H); 0.84 (t, J=7, 3H).

$^{13}$C-NMR: Major 200.7 (s); 175.3 (s); 121.5 (d); 49.2 (d); 41.1 (s); 35.2 (t); 34.5 (d); 30.3 (t); 29.0 (t); 26.5 (t); 24.9 (q); 23.3 (q); 21.8 (t); 13.0 (q). Minor 200.5 (s); 173.4 (s); 123.3 (d); 47.2 (d); 41.2 (s); 36.5 (t); 34.1 (d); 30.3 (t); 29.8 (t); 28.7 (t); 25.8 (q); 22.0 (q); 20.3 (t); 12.3 (q).

(+)-(4aR,7S)-8,8-dimethyl-7-ethyl-4,4a,5,6,7,8-hexahydro-2(3H)-naphthalenone: (+)-7c As above using (+)-6c. (+)-7c was obtained in 94% yield. $\alpha_D^{20}$ =+71.4.

g) Perhydro-7,8,8-trimethyl-2-naphthalenone: 8b (+)-(4aS,7R,8aS)-Perhydro-7,8,8-trimethyl-2-naphthalenone: (+)-8b A solution of enone (−)-7b (6.7g, 35 mmol) and tBuOH (2.6g, 35 mmol) in Et$_2$O (10 ml) was added to a mixture of Li (1.23 g, 175 mmol) in NH$_3$ (300 ml) at −78° C. After one hour, the temp. was equilibrated at 20° C., and after evaporation of NH$_3$, Et$_2$O (200 ml) was added followed by EtOH (5 ml) and saturated aqueous NH$_4$Cl (100 ml). The aqueous phase was extracted with Et$_2$O, the organic phase was washed to neutral with saturated aqueous NH$_4$Cl and then brine, dried (Na$_2$SO$_4$), filtered and concentrated. This mixture was diluted in CH$_2$Cl$_2$ (50 ml) and added dropwise to a suspension of PCC (9.1 g, 42 mmol) and SiO$_2$ (35 g) in CH$_2$Cl$_2$ (200 ml). After 4 hours at 20° C. Et$_2$O (300 ml) and Celite (150 g) were added and the reaction mixture was filtered over Celite. The funnel was well rinced with Et$_2$O and the filtrate was concentrated. Bulb-to-bulb distillation afforded pure ketone (+)-8b in 85% yield as a 4:1 mixture of (4aS,7R,8aS)1(4aR,7R,8aR) stereoisomers. Bp: 100° C./0.35 mbar. $\alpha_D^{20}$ =+13.0.

¹H-NMR: 2.45 (m, 1H); 2.31 (m, 2H); 2.10 (m, 1H); 1.97 (m, 1H); 1.76 (m, 1H); 1.56 (m, 1H); 1.45 (m, 1H); 1.36-1.13 (m, 4H); 1.02 (m, 1H); 0.87 (d, J=7, 3H); 0.86 (s, 3H); 0.72 (s, 3H).

¹³C-NMR: 213.3 (s); 52.9 (d); 42.1 (t); 41.7 (d); 41.1 (t); 36.5 (s); 36.1 (d); 34.3 (t); 33.5 (t); 30.4 (t); 26.0 (q); 16.4 (q); 13.4 (q).

(−)-(4aR,7S,8aR)-Perhydro-7,8,8-trimethyl-2-naphthalenone: (−)-8b

As above using (+)-7b. (−)-8b was obtained in 74% yield. $\alpha_D^{20}$ =−11.5.

h) Perhydro-7-ethyl-8,8-dimethyl-2-naphthalenone: 8c (−)-(4aS,7R,8aS)-Perhydro-7-ethyl-8,8-dimethyl-2-naphthalenone: (−)-8c A solution of enone (−)-7c (20.0 g, 97 mmol) and tBuOH (8.62 g, 117 mmol) in Et₂O (152 ml) was added to a mixture of Li (3.38 g, 485 mmol) in NH₃ (1000 ml) at −78° C. After 18 hours the temperature was equilibrated at 20° C., and after evaporation of NH₃, Et₂O (560 ml) was added followed by EtOH (14 ml) and saturated aqueous NH₄Cl (277 ml). The aqueous phase was extracted with Et₂O, the organic phase was washed to neutral with saturated aqueous NH₄Cl, then brine, dried (Na₂SO₄), filtered and concentrated. This mixture was diluted in CH₂Cl₂ (50 ml) and added dropwise to a suspension of PCC (30.9 g, 143 mmol) and Celite (46 g) in CH₂Cl₂ (200 ml). After 4 hours at 20° C. Et₂O (300 ml) and SiO₂ (50 g) were added and the reaction mixture was filtered over Celite. The funnel was well rinsed with Et₂O and the filtrate was concentrated. Bulb-to-bulb distillation afforded pure ketone (−)-8c in 25% yield as a 2:1 mixture of (4aS,7R,8aS)I(4aR,7R,8aR) stereoisomers. Bp: 150° C/0.1 mbar. $\alpha_D^{20}$ =−11.1.

¹H-NMR: 2.44 (m, 1H); 2.31 (m, 2H); 2.10 (m, 1H); 1.97 (m, 1H); 1.78 (m, 2H); 1.64-1.40 (m, 4H); 1.29 (m, 2H); 1.22-0.95 (m, 2H); 0.88 (s, 3H); 0.86 (t, J=7, 3H); 0.70 (s, 3H).

¹³C-NMR: Major 213.2 (s); 53.0 (d); 49.4 (d); 42.1 (t); 41.1 (t); 36.9 (s); 36.1 (d); 34.3 (t); 33.4 (t); 26.4 (t); 25.7 (q); 23.0 (t); 14.3 (q); 13.3 (q). Minor 213.1 (s); 47.1 (d); 46.5 (d); 42.0 (t); 41.5 (t); 36.3 (d); 36.1 (s); 34.2 (t); 27.2 (t); 27.0 (q); 22.9 (q); 22.4 (t); 18.8 (t); 13.0 (q).

(+)-(4aR,7S,8aR)-Perhydro-7-ethyl-8,8-dimethyl-2-naphthalenone: (+)-8c

As above using (+)-7c. (+)-8c was obtained in 35% yield as a 2:1 (4aR,7S,8aR)I(4aS,7S,8aS) mixture. $a_D^{20}$ =+11.3.

i) Ethyl 2- iperhydro-7,8,8-trimethyl-2-naphthalenyllidene1propano ate : (Z)-9b (+)-Ethyl (2Z,4aS,7R,8aS)-2-[perhydro-7,8,8-trimethyl-2-naphthalenylidene]propanoate: (+)-(Z)-9b EtONa (10 ml, 21% solution in EtOH, 31 mmol) was added dropwise to a mixture of ketone (+)-8b (5 g, 25.8 mmol) and triethylphosphonopropionate (7.4 g, 31 mmol) in pentane (50 ml). After 18 hours the mixture was poured onto ice, extracted with Et₂O, the organic phase was washed to neutral with brine, dried (Na₂SO₄), filtered, concentrated and bulb-to-bulb distilled to afford in 97% yield a 1.3:1 E/Z mixture of stereoisomers purified by CC (SiO₂, cyclohexane/Et₂O 98:2) to afford analytically pure Z and E stereoisomers. $\alpha_D^{20}$ =+12.53.

¹H-NMR: 4.10 (q, J=7, 2H); 3.18 (m, 1H); 2.61 (m, 1H); 1.86 (s, 3H); 1.79 (m, 2H); 1.60 (m, 1H); 1.52 (m, 1H); 1.37 (m, 2H); 1.31 (t, J=7, 3H); 1.19 (m, 2H); 1.00 (m, 2H); 0.92 (s, 3H); 0.88 (m, 1H); 0.84 (d, J=7, 3H); 0.68 (s, 3H).

¹³C-NMR: 170.8 (s); 148.3 (s); 119.5 (s); 60.2 (t); 54.1 (d); 42.2 (d); 37.5; (d); 36.4 (s); 35.6 (t); 34.1 (t); 32.6 (t); 31.0 (t); 30.7 (t); 26.3 (q); 16.4 (q); 15.3 (q); 14.4 (q); 13.6 (q).

(−)-Ethyl (2Z,4aR,7S,8aR)-2-[perhydro-7,8,8-trimethyl-2-naphthalenylidene]propanoate: (−)-(Z)-9b As above using (−)-8b. (−)-(Z)-9b: $\alpha_D^{20}$ =−8.5.

j) Ethyl (2Z)-2- iperhydro-7-ethyl,8 ,8-dimethyl-2-naphthalenylidenel propanoate: (Z)-9c (−)-Ethyl (2Z,4aS,7R,8aS)-2-[perhydro-7-ethyl,8,8-dimethyl-2-naphthalenylidene] propanoate: (−)-(Z)-9c EtONa (9 ml, 21% solution in EtOH, 28 mmol) was added dropwise to a mixture of ketone (+)-8c (4.8 g, 23 mmol) and triethylphosphonopropionate (6.66 g, 28 mmol) in pentane (48 ml). After 18 hours the mixture was poured onto ice, extracted with Et₂O, the organic phase was washed to neutral with brine, dried (Na₂SO₄), filtered, concentrated and bulb-to-bulb distilled to afford in 97% yield a 1.3:1 E/Z mixture of stereoisomers purified by CC (SiO₂, cyclohexane/Et₂O 99:1) to afford analytically pure a 3:1 (2Z,4aS,7R,8aS)1(2Z,4aR,7R,8aR) mixture of (Z)-stereoisomers. $\alpha_D^{220}$ =−5.9.

¹H-NMR: 4.19 (q, J=7, 2H); 3.18 (m, 1H); 2.62 (m, 1H); 1.86 (s, 3H); 1.79 (m, 2H); 1.67 (m, 4H); 1.51 (m, 1H); 1.36 (m, 2H); 1.31 (t, J=7, 3H); 1.03 (m, 4H); 0.94 (s, 3H); 0.86 (t, J=7, 3H); 0.66 (s, 3H).

¹³C-NMR: Major 170.7 (s); 148.4 (s); 119.4 (s); 60.2 (t); 54.2 (d); 50.0 (d); 37.6 (d); 36.8 (s); 35.6 (t); 34.0 (t); 31.0 (t); 32.6 (t); 26.6 (t); 26.0 (q); 23.0 (t); 15.3 (q); 14.4 (2q); 13.3 (q). Minor 170.8 (s); 148.1 (s); 119.5 (s); 60.2 (t); 47.9 (d); 47.7 (d); 37.7 (d); 36.0 (s); 35.5 (t); 32.4 (t); 31.1 (t); 27.8 (t); 27.4 (q); 23.1 (q); 22.7 (t); 18.9 (t); 15.3 (q); 14.4 (q); 13.1 (q).

(+)-Ethyl (2Z,4aR,7S,8aR)-2-[perhydro-7-ethyl,8,8-dimethyl-2-naphthalenylidene] propanoate: (+)-(Z)-9c As above using (+)-8c. (+)-(Z)-9c: $\alpha_D^{20}$ =+4.75. B.p.: 160° C./0.5 mbar.

k) Ethyl (2Z)-2-1perhydro-7,8,8 -trimethyl-2-naphthalenylidene 1butanoate: (Z)-9d (−)-Ethyl (2Z, 4aR,7S,8aR)-2-[perhydro-7,8,8-trimethyl -2-naphthalenylidene]butanoate: (−)-(Z)-9d EtONa 1.04 ml, 21% solution in EtOH, 3.22 mmol) was added dropwise to a mixture of ketone (−)-(7S)-8b (0.52 g, 2.68 mmol) and triethylphosphonobutyrate (0.67 g, 2.68 mmol) in pentane (10 ml). After 18 hours the mixture was poured onto ice, extracted with Et₂O, the organic phase was washed to neutrality with brine, dried (Na₂SO₄), filtered, concentrated and bulb-to-bulb distilled to afford in 90% yield a 1.5:1 E/Z mixture of stereoisomers, purified by CC (SiO₂, cyclohexane/Et₂O 95:5). $[\alpha]_D^{20}$ =−0.01 (c=2.5, CHCl₃).

¹H-NMR: 4.19 (q, J=7, 2H); 3.03 (m, 1H); 2.60 (m, 1H); 2.30 (q, J=7.4, 2H); 1.80 (m, 2H); 1.61 (m, 1H); 1.52 (m, 1H); 1.37 (m, 2H); 1.31 (t, J=7, 3H); 1.19 (m, 2H); 1.00 (m, 2H); 1.00 (t, J=7, 3H); 0.91 (s, 3H); 0.90 (m, 1H); 0.84 (d, J=7, 3H); 0.67 (s, 3H).

¹³C-NMR: 170.8 (s); 146.9 (s); 126.6 (s); 60.1 (t); 54.1 (d); 42.2 (d); 37.9 (d); 36.5 (s); 35.7 (t); 34.1 (t); 32.5 (t); 31.0 (t); 30.7 (t); 26.2 (q); 22.9 (t); 16.5 (q); 14.5 (q); 14.2 (q); 13.6 (q).

l) Ethyl (2E)-2-iperhydro-7,8,8-trimethyl-2-naphthalenylidenelpropanoate: (E)-9b (−)-Ethyl (2E,4aS,7R,8aS)-2-[perhydro-7,8,8-trimethyl-2-naphthalenylidene]propanoate: (−)-(E)-9b See (i) above. $\alpha_D^{20}$ =−18.23.

¹H-NMR:: 4.18 (q, J=7, 2H); 3.03 (m, 1H); 2.73 (m, 1H); 1.86 (s, 3H); 1.78 (m, 2H); 1.61 (m, 1H); 1.52 (m, 1H); 1.37 (m, 2H); 1.29 (t, J=7, 3H); 1.19 (m, 2H); 1.05 (m, 2H); 0.93 (s, 3H); 0.89 (m, 1H); 0.84 (d, J=7, 3H); 0.71 (s, 3H).

¹³C-NMR: 170.6 (s); 149.0 (s); 119.3 (s); 60.1 (t); 53.8 (d); 42.2 (d); 37.6 (d); 36.4 (s); 36.3 (t); 34.0 (t); 32.0 (t); 31.6 (t); 30.6 (t); 26.3 (q); 16.5 (q); 15.0 (q); 14.3 (q); 13.6 (q).

(+)-Ethyl (2E,4aR,7S,8aR)-2-[perhydro-7,8,8-trimethyl-2-naphthalenylidene] propanoate: (+)-(E)-9b As above using (−)-8b. (+)-(E)-9b: $\alpha_D^{20}$ =+21.36.

m) Ethyl (2E)-2-iperhydro-7-ethyl-8,8-dimethyl-2-naphthalenylidenelpropanoate: (E)-9c (−)-Ethyl (2E, 4aS, 7R,8aR)-2-[perhydro-7-ethyl-8,8-dimethyl-2-naphthalenylidene] propanoate: (−)-(E)-9c As above in (j) using (−)-8c. (−)-(E)-9c: $\alpha_D^{20}$ =−27.55.

$^1$H-NMR: 4.18 (q, J=7, 2H); 3.03 (m, 1H); 2.72 (m, 1H); 1.87 (m, 3H); 1.79 (m, 2H); 1.68 (m, 4H); 1.51 (m, 2H); 1.37 (m, 1H); 1.29 (t, J=7, 3H); 1.05 (m, 4H); 0.94 (t, J=7, 3H); 0.87 (m, 3H); 0.69 (s, 3H).

$^{13}$C-NMR: Major 170.6 (s); 149.1 (s); 119.3 (s); 60.1 (t); 54.0 (d); 49.9 (d); 37.6 (d); 36.8 (s); 36.3 (t); 33.9 (t); 32.1 (t); 31.7 (t); 26.6 (t); 26.1 (q); 23.0 (t); 15.0 (q); 14.4 (q); 14.3 (q); 13.3 (q). Minor 170.6 (s); 148.7 (s); 119.4 (s); 60.1 (t); 47.9 (d); 47.4 (d); 37.8 (d); 36.0 (s); 36.0 (t); 32.3 (t); 31.3 (t); 27.7 (t); 27.4 (q); 23.0 (q); 22.6 (t); 18.9 (t); 15.0 (q); 14.3 (q); 13.1 (q).

(+)-Ethyl (2E, 4aR, 7S,8aS)-2-[perhydro-7-ethyl-8,8-dimethyl-2-naphthalenylidene] propanoate: (+)-(E)-9c As above using (+)-8c. (+)-(E)-9c: $\alpha_D^{20}$ =+26.76. B.p.: 160° C./0.5 mbar.

n) Ethyl (2E)-2-lperhydro-7,8,8-trimethyl-2-naphthalenylidenelbutanoate: (E)-9d (+)-Ethyl (2E,4aR,7S,8aR)-2-[perhydro-7,8,8-trimethyl-2-naphthalenylidene]butanoate: (+)-(E)-9d See above in (k). $\alpha_D^{20}$ =+0.001 (neat).

$^1$1-NMR: 4.19 (q, J=7, 2H); 2.89 (m, 1H); 2.73 (m, 1H); 2.30 (q, J=7.4, 2H); 1.80 (m, 2H); 1.61 (m, 1H); 1.52 (m, 1H); 1.37 (m, 2H); 1.29 (t, J=7, 3H); 1.19 (m, 2H); 1.00 (m, 2H); 1.00 (t, J=7, 3H); 0.93 (s, 3H); 0.90 (m, 1H); 0.84 (d, J=3H), 0.70 (s, 3H).

$^{13}$C-NMR: 170.6 (s), 147.4 (s); 126.5 (s); 60.0 (t); 54.3 (d); 42.2 (d); 37.6 (d); 36.3 (s); 36.0 (t); 34.0 (t); 32.3 (t); 31.0 (t); 30.6 (t); 26.3 (q); 22.8 (t); 16.5 (q); 14.4 (q) ; 14.1 (q) ; 13.6 (q).

o) (2Z)-2-1Perhydro-7,8 ,8-trimethyl-2-naphthalenylidenel -1-propanol: (Z)-10b (+)-(2Z)-2-[(4aS,7R,8aS)-Perhydro-7,8,8-trimethyl-2-naphthalenylidene]-1-propanol: (+)-(Z)-10b A solution of ester (+)-(Z)-9b (400 mg, 1.44 mmol) in Et$_2$O (10 ml) was added dropwise to a suspension of LiAlH$_4$ (55 mg, 1.4 mmol) in Et$_2$O (2 ml). After 2 hours at 20° C., the reaction mixture was cooled to 0° C. and H$_2$O (0.7 ml), aqueous 15% NaOH (0.7 ml) and H$_2$O (0.21 ml) were successively added. After 30 minutes, the mixture was filtered, rinsed with Et$_2$O and the filtrate was concentrated and bulb-to-bulb distilled to afford pure (+)-(Z)-10b in 97% yield. Bp: 150° C./0.1 mbar, $[\alpha]_D^{20}$ =+0.7, (c=3.7, CHCl$_3$).

$^1$H-NMR: 4.20 (d, J=11.2, 1H); 4.08 (d, J=11.2, 1H); 2.84 (m, 1H); 2.60 (m, 1H); 1.86 (s, OH); 1.77 (s, 3H); 1.70 (m, 1H); 1.61 (m, 1H); 1.45 (m, 1H); 1.41-1.11 (m, 8H); 0.93 (s, 3H); 0.83 (d, J=7, 3H); 0.69 (s, 3H).

$^{13}$C-NMR: 138.6 (s); 123.9 (s); 63.5 (t); 54.5 (d); 42.2 (d); 37.7 (d); 36.4 (s); 35.8 (t); 34.3 (t); 30.7 (t); 30.4 (t); 30.2 (t); 26.4 (q); 16.4 (2q); 13.6 (q). (−)-(2Z)-2-[(4aR,7S,8aR)-Perhydro-7,8,8-trimethyl-2-naphthalenylidene]-1-propanol: (−)-(Z)-10b As above, using (−)-(Z)-9b. (−)-(Z)-10b was obtained in 98% yield. $[\alpha]_D^{20}$ =−0.5, (c=2.5, CHCl$_3$).

p) (2Z)-2- iPerhydro-7-ethyl-8,8-dimethyl-2-naphthalenylidenel-1-propanol: (Z)-10c (−)-(2Z)-2-[(4aS,7R,8aS)-Perhydro-7-ethyl-8,8-dimethyl-2-naphthalenylidene]-1-propanol: (−)-(Z)-10c A solution of ester (−)-(Z)-9c (500 mg, 1.7 mmol) in Et$_2$O (10 ml) was added dropwise to a suspension of LiA1H$_4$ (65 mg, 1.7 mmol) in Et$_2$O (2 ml). After 2 hours at 20° C., the reaction mixture was cooled to 0° C. and H$_2$O (0.7 ml), aqueous 15% NaOH (0.7 ml) and H$_2$O (0.2 ml) were successively added. After 30 minutes, the mixture was filtered, rinsed with Et$_2$O and the filtrate was concentrated and bulb-to-bulb distilled to afford pure (−)-(Z)-10c in 94% yield. Bp: 160° C./0.1 mbar, $\alpha_D^{20}$ =−14.4, (neat).

$^1$H-NMR: 4.20 (d, J=11.2, 1H); 4.08 (d, J=11.2, 1H); 2.83 (m, 1H); 2.60 (m, 1H); 1.77 (s, 3H); 1.68 (m, 2H); 1.61 (m, 2H); 1.47-1.28 (m, 8H); 1.26 (brs, OH); 1.05 (m, 1H); 0.94 (s, 3H); 0.87 (t, J=7, 3H); 0.67 (s, 3H).

$^{13}$C-NMR: Major 138.6 (s); 123.9 (s); 63.5 (t); 54.6 (d); 50.0 (d); 37.8 (d); 36.8 (s); 35.8 (t); 34.2 (t); 30.5 (t); 30.3 (t); 26.7 (t); 26.1 (q); 23.0 (t); 16.4 (q); 14.4 (q); 13.3 (q). Minor 138.5 (s); 124.0 (s); 63.5 (t); 48.0 (2d); 37.9 (d); 36.0 (s); 35.6 (t); 30.6 (t); 30.0 (t); 28.0 (t); 27.5 (q); 23.1 (q); 22.7 (t); 18.9 (t); 16.4 (q); 13.1 (q).

(+)-(2Z)-2- [(4aR,7S,8aR)-Perhydro-7-ethyl-8,8-dimethyl-2-naphthalenylidene] -1-propanol: (+)-(Z)-10c As above, using (+)-(Z)-9c. (+)-(Z)-10c was obtained in 98% yield. $[\alpha]_D^{20}$ =+15.7, (c=2.0, CHCl$_3$).

q) (2Z)-2-17,8,8-trimethyloctahydronaphthalen-2(1H)-ylidenel -1 -butanol: (Z)-10d (+)-(2Z)-2-[(4aR,7S,8aR)-7,8,8-trimethyloctahydronaphthalen-2(1H)-ylidene]-1-butanol: (+)-(Z)-10d A solution of ester (−)-(2Z,7S)-9d (600 mg, 2.05 mmol) in Et$_2$O (4 ml) was added dropwise to a suspension of LiAlH$_4$ (82 mg, 2.16 mmol) in Et$_2$O (6 ml). After 2h at 20° C., the reaction mixture was cooled to 0° C. and H$_2$O (0.8 ml), aqueous 15% NaOH (0.8 ml) and H$_2$O (0.24 ml) were successively added. After 30 min, the mixture was filtered, rinsed with Et$_2$O and the filtrate was concentrated and purified by CC/SiO$_2$ (cyclohexane/Et$_2$O 95:5) to afford pure (Z)- and (E)-10d in 54% yield $[\alpha]D^{20}$ =+10.6 (c=0.5, CHCl$_3$).

$^1$H-NMR: 4.19 (d, J=12.3, 1H); 4.10 (d, J=12.3, 1H); 2.83 (m, 1H); 2.59 (m, 1H); 2.17 (q, J=7.7, 2H); 1.86 (s, OH); 1.75 (m, 1H); 1.60 (m, 1H); 1.46 (m, 1H); 1.43-1.11 (m, 8H); 0.98 (t, J=7.7, 3H); 0.93 (s, 3H); 0.83 (d, J=7, 3H); 0.69 (s, 3H).

$^{13}$C-NMR: 139.2 (s); 130.8 (s); 61.8 (t); 54.7 (d); 42.3 (d); 37.8 (d); 36.4 (s); 36.4 (s); 34.3 (t); 30.7 (t); 30.4 (t); 30.1 (t); 26.4 (q); 24.0 (t); 16.4 (q); 14.3 (q); 13.6 (q).

r) (2E)-2-1Perhydro-7,8,8-trimethyl-2-naphthalenylidenel-l-propanol: (E)-10b (+)-(2E)-2-[(4aS,7R,8aS)-Perhydro-7,8,8-trimethyl-2-naphthalenylidene]-1-propanol: (+)-(E)-10b As above in (o) using (−)-(E)-9b. (+)-(E)-10b was obtained in 70% yield. Bp: 150° C./0.1 mbar. $[\alpha]_D^{20}$ =+1.5, (c=1.1, CHCl$_3$).

$^1$H-NMR: 4.13 (s, 2H); 2.72 (m, 2H); 1.78 (s, 3H); 1.72 (m, 1H); 1.60 (m, 1H); 1.46-1.09 (m, 8H); 0.94 (s, 3H); 0.92 (m, 2H); 0.84 (d, J=7, 3H); 0.70 (s, 3H).

$^{13}$C-NMR: 138.8 (s); 123.9 (s); 63.6 (t); 53.8 (d); 42.3 (d); 37.7 (d); 36.7 (t); 36.3 (s); 34.2 (t); 30.9 (t); 30.7 (t); 29.9 (t); 26.4 (q); 16.5 (q) ; 16.2 (q) ; 13.6 (q).

(−)-(2E)-2-[(4aR,7S,8aR)-Perhydro-7,8,8-trimethyl-2-naphthalenylidene]-1-propanol: (−)-(E)-lob As above, starting from (+)-(E)-9b. (−)-(E)-10b was obtained in 94% yield. $[\alpha]_D^{20}$ =−0.4, (c=2.2, CHCl$_3$).

s) (2E)-2- iPerhydro-7-ethyl-8,8-dimethyl-2-naphthalenylidenel -1-propanol: (E)-10c (−)-(2E)-2-[(4aS,7R,8aS)-Perhydro-7-ethyl-8,8-dimethyl-2-naphthalenylidene]-1-propanol: (−)-(E)-10c As above in (p) using (−)-(E)-9c. (−)-(E)-10c was obtained in 96% yield. Bp: 160° C./0.1 mbar. $[\alpha]_D^{20}$ =−13.1 (neat).

$^1$H-NMR: 4.12 (s, 2H); 2.71 (m, 2H); 1.77 (s, 3H); 1.69 (m, 2H); 1.64 (m, 2H); 1.54-1.26 (m, 8H); 1.16 (brs, OH); 1.03 (m, 1H); 0.95 (s, 3H); 0.87 (t, J=7, 3H); 0.68 (s, 3H).

$^{13}$C-NMR: Major 138.8 (s) ; 123.9 (s) ; 63.6 (t) ; 53.9 (d) ; 50.0 (d) ; 37.8 (d) ; 36.7 (s) ; 36.7 (t) ; 34.2 (t) ; 31.0 (t) ; 29.9 (t) ; 26.6 (t) ; 26.1 (q) ; 23.0 (t) ; 16.2 (q) ; 14.4 (q) ; 13.4 (q). Minor 138.7 (s) ; 123.9 (s) ; 63.6 (t) ; 48.0 (d) ; 47.3 (d) ; 38.0 (d) ; 36.4 (t) ; 35.9 (s) ; 30.7 (t) ; 30.1 (t) ; 27.9 (t) ; 27.4 (q) ; 23.1 (q) ; 22.7 (t) ; 18.9 (t) ; 16.2 (q) ; 13.1 (q).

(+)-(2E)-2-[(4aR,7S,8aR)-Perhydro-7-ethyl-8,8-dimethyl-2-naphthalenylidene]-1-propanol: (+)-(E)-10c As above, starting from (+)-(E)-9c. (+)-(E)-10c was obtained in 96% yield. $[\alpha]_D^{20}$ =+15.0, (c=2.0, CHCl$_3$).

t) (2E)-2-17,8,8-trimethyloctahydronaphthalen-2(1H)-ylidenel-1-butanol: (E)-10d (+)-(2E)-2-[(4aR,7S,8aR)-7,8,8-trimethyloctahydronaphthalen-2(1H)-ylidene]-1-butanol: (+)-(E)-10d As above in (q) using (+)-(E)-9d. (+)-(E)-10d was obtained in 95% yield.

$[\alpha]_D^{20}$ =+4.9 (c=0.9, CHCl$_3$).

$^1$H-NMR: 4.13 (AB, J=11.3, 4.8, 2H); 2.71 (m, 2H); 2.18 (q, J=7.3, 2H); 1.75 (m, 1H); 1.60 (m, 1H); 1.46-1.14 (m, 8H); 0.99 (t, J=7.3, 3H); 0.94 (s, 3H); 0.90 (m, 2H); 0.84 (d, J=7, 3H); 0.70 (s, 3H).

$^{13}$C-NMR: 139.2 (s); 130.8 (s); 61.9 (t); 54.3 (d); 42.3 (d); 37.8 (d); 36.7 (t); 36.4 (s); 34.3 (t); 30.7 (t); 30.5 (t); 30.0 (t); 26.4 (q); 23.8 (t); 16.5 (q); 14.2 (q); 13.6 (q).

u) Ethyl 2-(7,8,8-trimethyl-decahydronaphthalene-2-yl) propanoate: 11b (−)-Ethyl 2-((4aS,7S,8aR)-7,8,8-trimethyl-decahydronaphthalene-2-yl) propanoate: (−)-11b A solution of (+)-(2E,7S)-9b (5.0g, 0.027 mol) in EtOH (50 ml) was hydrogenated (570 ml H$_2$) over 5% Pd/C (250 mg) for 24h. The crude reaction mixture was filtered, concentrated and bulb-to-bulb distilled (120° C./0.17 mbar) to afford (−)-11b in 45% yield as a 1.1:1 mixture of diastereoisomers in α position of the ester. $[\alpha]_D^{20}$ =−1.3 (c=1.1, CHCl$_3$).

$^1$H-NMR: (main stereoisomer, deduced from the mixture) 4.13 (q, J=7, 2H) ; 2.24 (q, J=7, 1H) ; 1.67 (m, 2H) ; 1.56 (m, 2H) ; 1.25 (t, J=7, 3H) ; 1.18 (m, 2H) ; 1.10 (d, J=7, 3H) ; 1.0-0.7 (m, 8H) ; 0.87 (s, 3H) ; 0.82 (d, J=7, 3H) ; 0.63 (s, 3H).

$^{13}$C-NMR: (main stereoisomer, deduced from the mixture) 176.6 (s); 60.0 (t); 52.2 (d); 45.7 (d); 42.3 (d); 41.4 (d); 37.0 (d); 36.1 (s); 34.6 (t); 30.7 (t); 29.5 (t); 29.0 (t); 28.7 (t); 26.3 (q); 16.6 (q); 14.4 (q); 14.1 (q); 13.9 (q).

v) 2-(7,8,8-trimethyl-decahydronaphthalene-2-yl) propan-1-ol: 12b (−)-2-((4aS,7S,8aR)-7,8,8-trimethyl-decahydronaphthalene-2-yl) propan-1-ol: (−)-12b A solution of ester (−)-11b (2150 mg, 7 7 mmol) in Et$_2$O (10 ml) was added dropwise to a suspension of LiAlH$_4$ (290 mg, 7.7 mmol) in Et$_2$O (15 ml). After 1 h at 20° C., the reaction mixture was cooled to 0° C. and H$_2$O (0.3 ml), aqueous 15% NaOH (0.3 ml) and H$_2$O (0.9 ml) were successively added. After 30 min, the mixture was filtered, rinsed with Et$_2$O and the filtrate was concentrated and purified by bulb-to-bulb distillation (120° C./0.2 mbar) to afford 12b in 87% yield as a 1.1:1 mixture in α position of the carbinol.

$[\alpha]_D^{20}$ =−0.73 neat $^1$H-NMR: (main stereoisomer, deduced from the mixture) 3.6 (m, 1H); 3.45 (m, 1H); 1.83 (m, 1H); 1.68 (m, 2H); 1.57 (m, 2H); 1.35 (m, 1H); 1.19 (m, 1H); 0.97 (m, 2H); 0.95-0.70 (m, 7H); 0.91 (d, J=7, 3H); 0.87 (s, 3H); 0.83 (d, J=7, 3H); 0.64 (s, 3H).

$^{13}$C-NMR: (main stereoisomer, deduced from the mixture) 66.3 (t); 52.4 (d); 42.5 (d); 41.1 (d); 40.1 (d); 37.3 (d); 36.2 (s); 35.3 (t); 34.7 (t); 30.8 (t); 30.3 (t); 28.8 (t); 26.4 (q); 16.5 (q); 13.9 (q); 13.2 (q).

Example 2

Preparation of a Perfuming Composition

An eau de toilette for women was prepared by admixing the following ingredients:

| Ingredient | Parts by weight |
| --- | --- |
| Phenylethyl acetate | 5 |
| 10%* C 11 Aldehyde undecylenic | 10 |
| 10%* Cuminic aldehyde | 15 |
| Benzyl benzoate | 290 |
| 4-Phenyl-2-butanone | 5 |
| Citronellol | 80 |
| (1'R,E)-2-ethyl-4-(2',2',3'-trimethyl-3'-cyclopenten-1'-yl)-2-buten-1-ol | 10 |
| 10%* 1-(2,6,6-trimethyl-1-cyclohexen-1-yl)-2-buten-1-one | 20 |
| Phenylethyl formiate | 10 |
| Geraniol | 60 |
| Geranium essential oil | 30 |
| Gurjun baume | 480 |
| Ionone Beta | 5 |
| Linalool | 25 |
| 10%* Methyl Heptinecarbonate | 15 |
| 10%* Methyl isoeugenol | 20 |
| 10%* Mousse Cristal | 15 |
| 1%* Rose oxide | 10 |
| Patchouli essential oil | 20 |
| Phenethylol | 490 |
| 10%* Phenylethyle phenylacetate | 25 |
| (2-Methoxyethyl)benzene | 5 |
| Allspice essence | 10 |
| 10%* Rosinol | 20 |
| 10%* Safranal | 10 |
| 10%* Methyl salicylate | 5 |
| Tonalide ®[1] | 10 |
| | 1700 |

*in dipropyleneglycol
[1](5,6,7,8-tetrahydro-3,5,5,6,8,8-hexamethyl-2-naphthyl)-1-ethanone; origin PFW, Holland The addition of 300 parts by weight of (2E)-2-[(4aR,7S,8aR)-perhydro-7,8,8-trimethyl-2-naphthalenylidene]-1-propanol to the above-described perfuming composition imparted a warm, very natural woody-sandalwood milk effect, similar to the one obtained when instead of the invention's compound it was added the same amount of Santal Mysore essential oil.

When to the above composition there was added the same amount of a sandalwood odorant of the campholenic family, the perfume obtained was much more aggressive, harsh and without the warm and the soft milky character provided by the natural sandalwood oil or the invention's compound.

Example 3

Preparation of a Perfuming Composition

An eau de toilette for men was prepared by admixing the following ingredients:

| Ingredient | Parts by weight |
| --- | --- |
| 1,1-Dimethyl-2-phenylethyl acetate | 20 |
| Cinnamyl acetate | 5 |
| Geranyl acetate | 50 |
| Cinnamic alcohol | 150 |

-continued

| Ingredient | Parts by weight |
| --- | --- |
| 3-Phenyl-1-propanol | 150 |
| 10%* Ambrinol | 75 |
| 50%* Benjoin essential oil | 700 |
| Benzyl benzoate | 300 |
| 10%* Methyl benzoate | 15 |
| Cinnamon essential oil | 30 |
| Cardamone essential oil | 130 |
| Cedar essential oil | 325 |
| 10%* Cetalox ®[1] | 30 |
| 10%* Cis-3-Hexenol | 10 |
| 50%* Ciste absolute | 150 |
| Citronellol | 80 |
| Copahu essential oil | 60 |
| Coumarine | 20 |
| 10%* Cumin | 30 |
| Cypressessential oil | 70 |
| 10%* Fennel oil | 20 |
| *Gaiacum* essential oil | 20 |
| Geraniol | 10 |
| Glove essential oil | 440 |
| Hedione ®[2] | 100 |
| 1,3-Benzodioxole-5-carbaldehyde | 40 |
| Hivernal ®[3] | 20 |
| 10%* Indol | 10 |
| 10%* Ionone Beta | 25 |
| Lavander essential oil | 250 |
| Alpha iso methyl ionone | 10 |
| Nutmeg essential oil | 100 |
| Patchouli essential oil | 10 |
| Phenethylol | 180 |
| Phenylethyl phenylacetate | 55 |
| 10%* Ethyl phenylacetate | 10 |
| Bulgarian rose essential oil | 20 |
| 10%* 2,2,2-Trichloro-1-phenylethyle acetate | 75 |
| Vanilline | 5 |
| | 3800 |

*in dipropyleneglycol
[1]dodecahydro-3a,6,6,9a-tetramethyl-naphtho[2,1-b]furan; origin: Firmenich SA, Switzerland
[2]methyl dihydrojasmonate; origin: Firmenich SA, Switzerland
[3]3-(3,3/1,1-dimethyl-5-indanyl)propanal; origin: Firmenich SA, Switzerland The addition of 200 parts by weight of (2E)-2-[(4aR,7S, 8aR)-perhydro-7,8,8-trimethyl-2-naphthalenylidene]1-1-propanol to the above-described perfuming composition imparted a very nice, natural, warm sandalwood milky note.

Example 4

Preparation of a Perfuming Composition

A sandalwood perfume was prepared by admixing the following ingredients:

| Ingredient | Parts by weight |
| --- | --- |
| 1%* Borneol | 10 |
| Citronellol | 10 |
| (2-Methoxyethyl)benzene | 70 |
| 0.1%* 2-Methoxy-4-methylphenol | 35 |
| Furfural | 20 |
| 1%* Methylacetophenone | 35 |
| Isopropyl myristate | 2320 |
| 10%* Opoponax | 300 |
| Sandalwood essential oil | 1200 |
| | 4000 |

*in dipropyleneglycol

The addition of 1000 parts by weight of (2E)-2-[(4aR,7S, 8aR)-perhydro-7,8,8-trimethyl-2-naphthalenylidene]-1-propanol to the above-described perfuming composition imparted a clear sandalwood Mysore aspect which was not obtained by the addition of any of the known sandalwood odorants of the perfumer's palette.

What is claimed is:

1. A compound having the formula

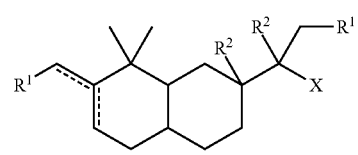

(I)

wherein
one dotted line represents a carbon-carbon single bond and the other a carbon-carbon single bond or double bond;
X represents a $CH_2OH$ group or a CHO group;
each $R^1$ represents a hydrogen atom or a methyl group; and
the $R^2$, taken separately, represent each a hydrogen atom or the two $R^2$ groups, taken together, represent a $CH_2$ group or a carbon-carbon double bond;
with the compound being in the form of any one of its stereoisomers or a mixture thereof.

2. A perfuming composition comprising:
i) at least one compound of claim 1;
ii) at least one ingredient selected from the group consisting of a perfumery carrier and a perfumery base; and
iii) optionally at least one perfumery adjuvant.

3. The perfuming composition according to claim 2, wherein the compound has the formula

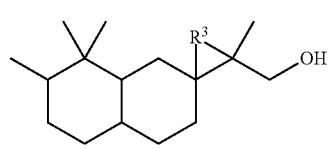

(III)

wherein $R^3$ represents a $CH_2$ group or a carbon-carbon bond.

4. A compound which is 2E)-2-[(4aR,7S,8aR)-perhydro-7,8,8-trimethyl-2-naphthalenylidene]-1-propanol.

5. A perfumed article comprising:
i) at least one compound of claim 1; and
ii) a consumer product base.

6. The perfumed article according to claim 5, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

7. The perfumed article according to claim 5, wherein the compound has the formula

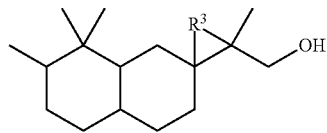 (III)

wherein $R^3$ represents a $CH_2$ group or a carbon-carbon bond.

8. The perfumed article according to claim 5, wherein the compound is 2-[perhydro-7,8,8-trimethyl-2-naphthalenylidene]-1-propanol, (2E)-2-[(4aR,7S,8aR)-perhydro-7,8,8-trimethyl-2-naphthalenylidene]-1-propanol or (2E)-2-[(4aS,7R,8aS)-perhydro-7,8,8-trimethyl-2-naphthalenylidene]-1-propanol.

9. The compound of claim 1, having the formula

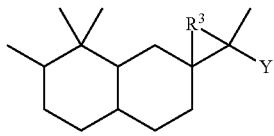 (V)

wherein $R^3$ represents a $CH_2$ group or a carbon-carbon bond; and

Y represents $CH_2OH$ or CHO group.

10. The compound of claim 1, which is 2-[perhydro-7,8,8-trimethyl-2-naphthalenylidene]-1-propanol, (2E)-2-[4aR,7S,8aR)-perhydro-7,8,8-trimethyl-2-naphthalenylidene]-1-propanol or (2E)-2-[(4aS,7R,8aS)-perhydro-7,8,8-trimethyl-2-naphthalenylidene]-1-propanol.

11. A method to confer, enhance, improve or modify the odor properties of a perfuming composition or of a perfumed article, which method comprises adding to the composition or article an effective amount of at least one compound of claim 4.

12. A perfumed article comprising:
iii) at least one compound of claim 4; and
iv) a consumer product base.

13. A method to confer, enhance, improve or modify the odor properties of a perfuming composition or of a perfumed article, which method comprises adding to the composition or article an effective amount of at least one compound of claim 1.

14. The method according to claim 13, wherein the compound has the formula

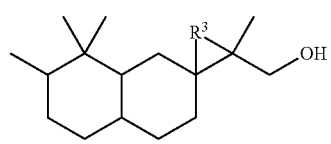 (III)

wherein $R^3$ represents a $CH_2$ group or a carbon-carbon bond.

15. The method according to claim 13, wherein the compound is 2-[perhydro-7,8,8-trimethyl-2-naphthalenylidene]-1-propanol, (2E)-2-[(4aR,7S,8aR)-perhydro-7,8,8-trimethyl-2-naphthalenylidene]-1-propanol or (2E)-2-[(4aS,7R,8aS)-perhydro-7,8,8-trimethyl-2-naphthalenylidene]-1-propanol.

16. The perfumed article according to claim 12, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *

UNITED STATES PATENT AND TRADEMARK OFFICE
CERTIFICATE OF CORRECTION

PATENT NO. : 8,481,013 B2
APPLICATION NO. : 13/123776
DATED : July 9, 2013
INVENTOR(S) : Chapuis Page 1 of 1

It is certified that error appears in the above-identified patent and that said Letters Patent is hereby corrected as shown below:

<u>Title Page:</u>
Item (73) Assignee, after "Firmenich SA," change "Geneav" to -- Geneva --.

Signed and Sealed this
Twentieth Day of August, 2013

Teresa Stanek Rea
*Acting Director of the United States Patent and Trademark Office*